(12) United States Patent
Back et al.

(10) Patent No.: US 12,157,714 B2
(45) Date of Patent: Dec. 3, 2024

(54) KETO-AMMONIUM COMPOUNDS

(71) Applicant: SPECIALTY OPERATIONS FRANCE, Lyons (FR)

(72) Inventors: Olivier Back, Lyons (FR); Sergio Mastroianni, Lyons (FR)

(73) Assignee: SPECIALTY OPERATIONS FRANCE, Lyons (FR)

(*) Notice: Subject to any disclaimer, the term of this patent is extended or adjusted under 35 U.S.C. 154(b) by 422 days.

(21) Appl. No.: 17/781,308

(22) PCT Filed: Nov. 27, 2020

(86) PCT No.: PCT/EP2020/083626
§ 371 (c)(1),
(2) Date: May 31, 2022

(87) PCT Pub. No.: WO2021/105356
PCT Pub. Date: Jun. 3, 2021

(65) Prior Publication Data
US 2023/0026924 A1   Jan. 26, 2023

(30) Foreign Application Priority Data
Nov. 29, 2019  (EP) ..................................... 19306538

(51) Int. Cl.
*C07C 225/06* (2006.01)
*C07D 211/74* (2006.01)

(52) U.S. Cl.
CPC .......... *C07C 225/06* (2013.01); *C07D 211/74* (2013.01)

(58) Field of Classification Search
CPC ............................ C07C 225/06; C07D 211/74
See application file for complete search history.

(56) References Cited

U.S. PATENT DOCUMENTS

| | | | |
|---|---|---|---|
| 2,863,872 A | 12/1958 | Silverstone et al. | |
| 5,851,982 A | 12/1998 | Sakata et al. | |
| 5,858,960 A | 1/1999 | Conroy et al. | |
| 2018/0093936 A1 | 4/2018 | Back et al. | |
| 2019/0292131 A1* | 9/2019 | Back ..................... | C07C 215/18 |

FOREIGN PATENT DOCUMENTS

| CN | 107353216 A | 11/2017 |
|---|---|---|
| DE | 1149363 B | 5/1963 |
| DE | 3402146 A1 | 7/1985 |
| EP | 721936 A1 | 7/1996 |
| GB | 941752 A | 11/1963 |
| WO | 9708284 A1 | 3/1997 |
| WO | 2018087181 A1 | 5/2018 |

OTHER PUBLICATIONS

E. K. Oikonomou, F. Mousseau, N. Christov, G. Cristobal, A. Vacher, M. Airiau, C. Bourgaux L. Heux, J.-F. Berret—Fabric Softener—Cellulose Nanocrystal Interaction: A Model for Assessing Surfactant Deposition on Cotton—J. Phys. Chem. B 2017, 121, 10, 2299-2307—doi: 10.1021/acs.jpcb.7b00191 (13 pages).
International Search Report issued in corresponding European Application No. PCT/EP2020/083626 dated Nov. 2, 2021, (4 pages).
Written Opinion issued in corresponding European Application No. PCT/EP2020/083626 dated Nov. 2, 2021 (5 pages).

* cited by examiner

*Primary Examiner* — Timothy R Rozof
(74) *Attorney, Agent, or Firm* — Osha Bergman Watanabe & Burton LLP

(57) ABSTRACT

The invention concerns new keto-ammonium compounds with surfactant properties and improved biodegradability.

14 Claims, No Drawings

KETO-AMMONIUM COMPOUNDS

The present application is a U.S. national stage entry under 35 U.S.C. § 371 of International Application No. PCT/EP2020/083626 filed on Nov. 27, 2020, which claims priority to European application No. 19306538.0 filed on Nov. 29, 2019, the entire contents of which are incorporated herein by reference for all purposes.

The present invention relates to new keto-ammonium compounds, in particular new keto-ammonium compounds derived from internal ketones obtained from fatty acids or their derivatives and the use of the new compounds as surfactants.

Fatty ammonium compounds which have surfactant properties and can be used in respective applications have been described in the literature and are available commercially in a variety of different types from various suppliers.

WO 97/08284 discloses compositions comprising Guerbet alcohol betaine esters which are represented by the general formula

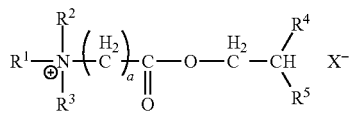

in which $R^1$ to $R^3$ are independently selected from $C_1$ to $C_4$ alkyl groups or $C_2$-$C_4$ alkenyl groups, a is from 1 to 4 and $R^4$ and $R^5$ are independently selected from $C_{12}$ to $C_{22}$ alkyl or alkenyl groups, the sum of chain lengths of $R^4$ and $R^5$ preferably being at least 30. Since the compounds are derived form Guerbet alcohols, the number of carbon atoms in groups $R^4$ and $R^5$ differs always by 2.

EP 721 936 is related to liquid quaternary ammonium compounds of the general formula

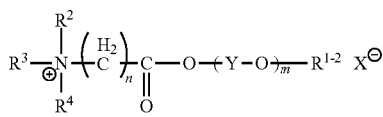

wherein $R^{1-2}$ is a linear or branched $C_{36}$-$C_{44}$ alkyl or alkenyl group, $R^2$ to $R^4$ are $C_1$-$C_5$ alkyl or hydroxyalkyl groups, Y is a linear or branched $C_2$-$C_4$ alkylene group, m is a number of 0 to 20 and n is an integer of 1 to 6. Preferred compounds of EP 721 936 are, as in WO 97/08284, derived from Guerbet alcohols and are represented by the formula

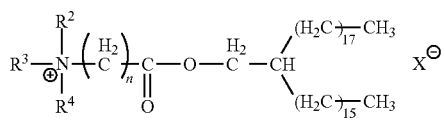

DE 3402146 relates to quaternary ammonium compounds. As in WO 97/08284 and EP 721936, the compounds comprise two long chain substituents which are esters of Guerbet acids.

WO 2018/087181, in its paragraphs [00161]-[00199], describes amine compounds of formulae

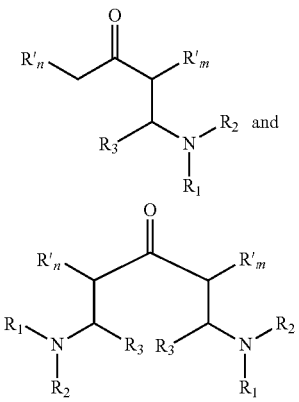

wherein $R_1$ and $R_2$ independently represent hydrogen, a linear or branched hydrocarbon radical having 1 to 24 carbon atoms which can be optionally substituted and/or interrupted by one or more heteroatoms or heteroatom containing groups, an ethylamine or [poly(ethylenimine)] ethylamine radical, a hydroxyethyl radical, a [poly(ethylenimine)]ethanol radical or a N,N-dialkylaminoalkyl radical and wherein $R_1$ and $R_2$ can also form an alkanediyl radical; $R_3$ represents hydrogen, a linear or branched hydrocarbon radical having 1 to 24 carbon atoms which can be optionally substituted and/or interrupted by one or more heteroatoms or heteroatom containing groups or an aromatic or heterocyclic radical which can be optionally substituted by one or more branched or linear hydrocarbon radicals which can optionally contain one or more heteroatoms; and $R'_n$ and $R'_m$ independently represent an aliphatic group. WO'181 further describes, in its paragraphs [00193]-[00200], the quaternization reaction of the above amine compounds to afford quaternary ammonium salts of formulae

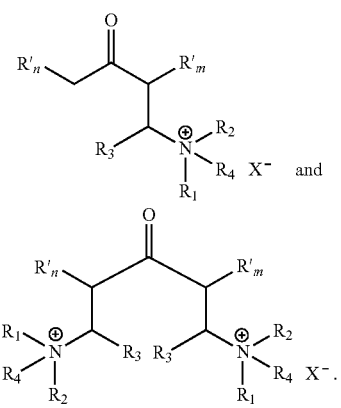

using an alkylating agent of formula $R_4X$, wherein $R_4$ represents a linear or branched hydrocarbon radical having 1 to 10 carbon atoms which can be optionally substituted and/or interrupted by a substituted or unsubstituted aromatic group and/or a heteroatom or heteroatom containing group (such as —$CH_3$, —CH—$CH_2CH_3$, benzyl or furfuryl) and wherein X is a leaving group (such as chlorine). While WO'181 might at most generally suggest through its paragraph [00440] or [00480] that the above quaternary ammonium salts could perhaps have some surfactant properties, WO'181 remains totally silent about the ability to biodegrade which such fatty quaternary ammonium compounds could or could not not exhibit. Furthermore, the Applicant synthesized these fatty quaternary ammonium compounds and observed that they were unstable, which, from a practical standpoint, makes them unsuitable for use as surfactants: they underwent decomposition at room temperature, releasing an ammonium compound of formula $R_1R_2R_4NHX$, e.g. trimethylammonium chloride, which was evil-smelling.

While fatty quaternary ammonium compounds are widely used as surfactants, there is still a need for compounds of this type having a good combination of surfactant properties on one hand and biodegradability on the other hand. Biodegradability has become more and more important in the recent past due to the desire of customers to have more environmentally friendly products. The improvement in biodegradability should, however, not negatively affect the surfactant properties.

It was thus an object of the present invention to provide new ammonium compounds with good surfactant properties and a good biodegradability.

This object is achieved with the compounds of formula (I).

Preferred embodiments of the present invention are set forth in the dependent claims and in the detailed specification hereinafter.

The novel ionic compounds in accordance with the present invention have the general formula (I)

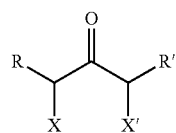

(I)

wherein R and R', which may be the same or different at each occurrence, are a $C_4$-$C_{27}$ aliphatic group,
X is a monovalent radical represented by formula (II)

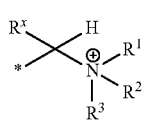

(II)

wherein $R^1$ and $R^2$, which may be the same or different, are hydrogen or
a $C_1$ to $C_4$ alkyl group,
$R^3$ is hydrogen,
$R^x$ is hydrogen or an aliphatic group of 1 to 6 carbon atoms, and wherein * denotes the position through which the monovalent radical is bound to the rest of the ionic compound,
X' is hydrogen or is a monovalent radical represented by formula (II) or wherein X and X' together form a divalent radical of formula (III)

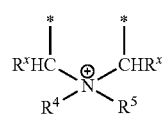

(III)

wherein $R^x$, which may be the same or different, are hydrogen or an aliphatic group with 1 to 6 carbon atoms, and
$R^4$ and $R^5$, which may be the same or different, are hydrogen or a $C_1$ to
$C_4$ alkyl group, and
wherein * denote the positions through which the divalent radical is bound to the rest of the ionic compound.

The aliphatic groups R and R' may be free of any double bond and of any triple bond. Alternatively, the aliphatic groups R and/or R' may comprise at least one —C═C— double bond and/or at least one —C≡C-triple bond.

The aliphatic groups R and R' are advantageously chosen from alkyl groups, alkenyl groups, alkanedienyl groups, alkanetrienyl groups and alkynyl groups.

The aliphatic groups R, respectively R', may be linear or branched.

Preferably, the aliphatic groups R and R' are independently chosen from alkyl and alkenyl groups.

More preferably, the aliphatic groups R and R' are both independently chosen from alkyl and alkenyl groups, generally from $C_4$-$C_{24}$ alkyl and $C_4$-$C_{24}$ alkenyl groups, very often from $C_4$-$C_{20}$ alkyl and $C_4$-$C_{20}$ alkenyl groups and often from (i) $C_4$-$C_{18}$ alkyl and $C_4$-$C_{18}$ alkenyl groups or from (ii) $C_4$-$C_{16}$ alkyl and $C_4$-$C_{16}$ alkenyl groups. More preferably, R and R' represent an alkyl group, generally a $C_4$-$C_{24}$ alkyl group, very often a $C_4$-$C_{20}$ alkyl group, often a $C_4$-$C_{18}$ alkyl group or a $C_4$-$C_{16}$ alkyl group.

Aliphatic groups R and R' with 6 to 24, preferably with 8 to 24, more preferably with 8 to 20, still more preferably with 10 to 20 and the most preferably with 10 to 16 carbon atoms have been found advantageous in certain cases. In particular, alkyl and alkenyl groups with 6 to 24, preferably with 8 to 24, more preferably with 8 to 20, still more preferably with 10 to 20 and the most preferably with 10 to 16 carbon atoms have been found advantageous as R and R' groups. More particularly, alkyl groups with 6 to 24, preferably with 8 to 24, more preferably with 8 to 20, still more preferably with 10 to 20 and the most preferably with 10 to 16 carbon atoms have been found advantageous as R and R' groups.

Acyclic aliphatic groups, more preferably linear aliphatic groups, still more preferably linear alkyl groups may be mentioned as preferred examples of substituents R and R'.

The number of carbon atoms of R or R' can be even or odd and each group R and R' can have the same number of carbon atoms or the number of carbon atoms of groups R and R' may be different.

If $R^x$ is an aliphatic group, it may be free of any double bond and of any triple bond. Alternatively, the aliphatic groups $R^x$ may comprise at least one —C═C— double bond and/or at least one —C≡C— triple bond.

In accordance with a preferred embodiment, $R^x$ is hydrogen.

The ionic compounds in one embodiment of the present invention comprise one substituent X represented by formula (II) above and hydrogen as substituent X'.

In this embodiment, $R^1$ and $R^2$, which may be the same or different, are hydrogen or a $C_1$ to $C_4$ alkyl group, preferably methyl or ethyl, more preferably methyl. Preferably at least one of $R^1$ and $R^2$ is, more preferably both $R^1$ and $R^2$ are, a $C_1$ to $C_4$ alkyl group, preferably methyl or ethyl, most preferably methyl. $R^3$ is hydrogen.

In accordance with another preferred embodiment of the present invention, X and X' are both represented by formula (II).

In this other embodiment, $R^1$ and $R^2$, which may be the same or different, are hydrogen or a $C_1$ to $C_4$ alkyl group, preferably methyl or ethyl, more preferably methyl. Preferably at least one of $R^1$ and $R^2$ is, more preferably both $R^1$ and $R^2$ are, a $C_1$ to $C_4$ alkyl group, preferably methyl or ethyl, most preferably methyl. $R^3$ is hydrogen.

In accordance with a third preferred embodiment of the present invention, X and X' form together a divalent radical of formula (III)

(III)

wherein $R^x$, which may be the same or different at each occurrence, are hydrogen or an aliphatic group of 1 to 6 carbon atoms, $R^4$ and $R^5$, which may be the same or different, are hydrogen or a $C_1$ to $C_4$ alkyl group, and wherein * denote the positions through which the divalent radical is bound to the rest of the ionic compound.

$R^4$ and $R^5$, which may be the same or different, are hydrogen or a $C_1$ to $C_4$ alkyl group; preferably, at least one of $R^4$ and $R^5$ is an alkyl group (most preferably a methyl group) and more preferably $R^4$ and $R^5$ are both alkyl groups (most preferably methyl groups).

Preferred compounds of the present invention are represented by the following formulae I' to I''':

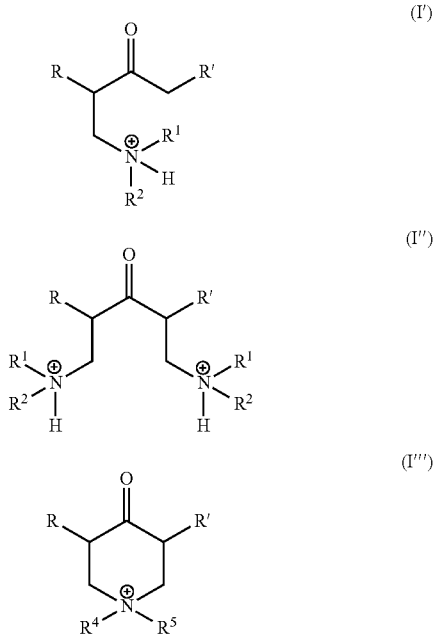

wherein R, R', $R^1$, $R^2$, $R^4$ and $R^5$ have the meaning as defined in claim 1 and described hereinbefore. Preferably, $R^1$, $R^2$, $R^4$ and $R^5$ are methyl.

Another embodiment of the present invention is directed to electroneutral compounds of formula (IV)

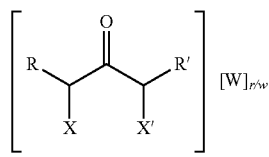

(IV)

wherein R, R', X and X' are as defined and described hereinbefore, W is an anion or an anionic group bearing w negative charges and r is the number of charges carried by the substituents X and X' which are represented by a group of formula (II) or (Ill).

Suitable anions or anionic groups W are e.g. halides such as chloride, fluoride, bromide or iodide, methyl sulfate or methosulfate anion ($CH_3$—$OSO_3^-$), sulfate anion, hydrogensulfate anion ($HSO_4^-$), carbonate anion ($CO_3^{2-}$), hydrogencarbonate anion ($HCO_3^-$) or an organic carboxylate anion such as acetate, propionate, benzoate, tartrate, citrate, lactate, glyoxylate, glycolate, gluconate, maleate, fumarate or succinate.

The compounds in accordance with the present invention can be obtained by a variety of different methods. Preferred processes for the manufacture of the compounds of the present invention include the reaction of an internal ketone of formula R—$CH_2$—C(=O)—$CH_2$—R', which internal ketone may preferably be obtained by decarboxylative ketonization of a fatty acid, a fatty acid derivative or a mixture thereof. A suitable process for the manufacture of internal ketones following this route is disclosed in US 2018/0093936 to which reference is made for further details.

The number of carbon atoms of the groups R and R' in compounds of formula (I) are preferably any of the following couples if the internal ketones used as reactant in the exemplary processes described hereinbefore are obtained from natural fatty acids having an even number of carbon atoms (4,4), (6,6), (8,8), (10,10), (12,12), (14,14), (16,16)
(6,8), (6,10), (6,12), (6,14), (6,16)
(8,10), (8,12), (8,14), (8,16)
(10,12), (10,14), (10,16)
(12,14), (12,16)
(14,16)

If the internal ketone is derived from fatty acids comprising an odd number of carbon atoms, other couples are possible and will be obtained.

The synthesis of the compounds of the present invention using internal ketones obtainable as indicated above as starting materials can preferably be carried out using a so called Mannich reaction or Mannich condensation as the first step.

The Mannich reaction is an organic reaction which consists of an amino alkylation taking place on a carbon linked to at least one hydrogen atom and adjacent to a carbonyl functional group by condensation between an enolizable carbonyl group containing substrate (e.g. ketone or aldehyde) and an aldehyde and a primary or secondary amine or ammonia. The final product is a #-amino-carbonyl compound also known as a Mannich base.

In the Mannich reaction, primary or secondary amines or ammonia, are employed for the activation of the aldehyde. Tertiary amines lack a N—H bond to form the intermediate electrophilic iminiums and are thus usually not employed.

The mechanism of the Mannich reaction starts with the formation of an electrophilic iminium ion from the amine and the aldehyde (for formaldehyde as activating aldehyde $R^x$ would be hydrogen):

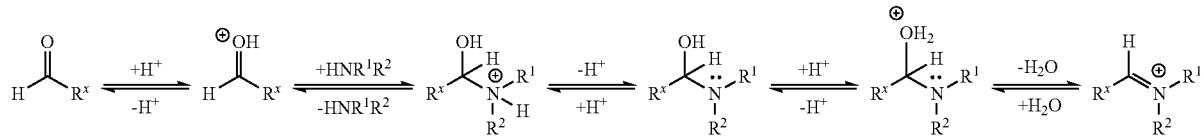

wherein $R^x$, $R^1$ and $R^2$ are as defined in claim 1.

In the second step, a compound with a carbonyl functional group (in the present case the internal ketone) after tautomerization to the nucleophilic enol form attacks the iminium ion to form the final product of the Mannich condensation reaction:

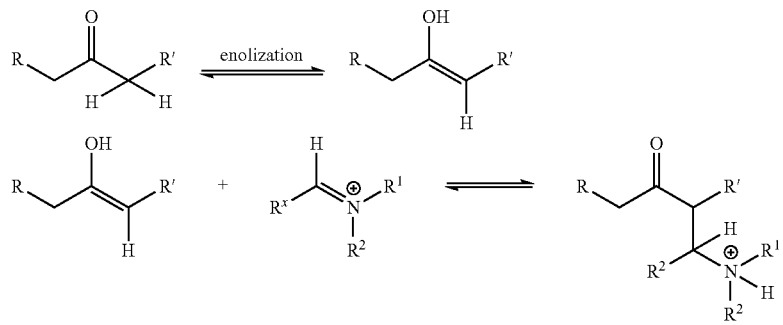

wherein R, R', $R^1$ and $R^2$ have the meaning as defined in claim 1.

Although formaldehyde (methylene oxide, for which $R^x$ is hydrogen) is preferably employed in Mannich reactions, other aldehydes may be used in which case the reaction should be more generally defined as an aminoalkylation instead of aminomethylation.

Commercial formaldehyde sources exist in different forms, all of them can be used in the purpose of conducting the Mannich reaction. Formaldehyde can be directly used as a gas or in the form of an aqueous formaldehyde solution (frequently referred to as "formalin"). In this aqueous solution formaldehyde molecules in the monomeric state are present together with oligomers usually having a degree of polymerization of 10 or less. Other sources of formaldehyde are: 1,3,5-trioxane which is a solid cyclic trimer of formaldehyde easily decomposed to formaldehyde by acids or by heating in organic solvents or paraformaldehyde which is a crystalline polymer with a degree of polymerization usually below 50 which becomes water soluble after depolymerization which is usually achieved by heating.

In some cases aqueous formaldehyde (35-40% w/w) solution has been proved advantageous in Mannich reactions and is also preferred for the manufacture of the compounds in accordance with the present invention.

Alternatively, reactants that are able to readily decompose to formaldehyde in situ can be employed. In this case preferred reactants are 1,3-dioxolane that decomposes by reaction with water into formaldehyde and glycol, dimethoxymethane that decomposes by reaction with water into formaldehyde and methanol, diethoxyethane that decomposes by reaction with water into formaldehyde and ethanol.

If an aldehyde $R^x$—CHO instead of formaldehyde is used, the carbon atom connecting the nitrogen atom of the amine used to the carbon adjacent to the carbonyl group of the substrate carries one hydrogen atom and one group $R^x$ stemming from the aldehyde reactant.

The presence of aldehyde in a Mannich reaction makes it possible to connect the carbonyl containing substrate and the amine moieties through a methylene group (if formaldehyde is used as activating aldehyde) or through an alkylene group —$CHR^x$—.

When aldehydes other than formaldehyde are used as activating aldehydes, a reactivity decrease is often observed due to the enhanced steric requirements and the lower electrophilicity of the aminoalkylating agent. Furthermore, the stereochemistry of the resultant product is affected through the creation of a chiral center in the molecule. If other chiral centers are present in the carbonyl containing substrate or the amine used or if the reactive center of the internal ketone substrate is prochiral, the formation of several diastereoisomers takes place.

When using internal ketones of formula R—$CH_2$—C(=O)—$CH_2$—R' as starting materials for the Mannich reaction, there are two methylene groups which are available for the reaction and thus normally a mixture of keto-monoamine compounds (such as e.g. compounds of formula (I')) and keto-diamine compounds (such as e.g. compounds of formula (I")) is obtained. The ratio of keto-monoamine compounds to keto-diamine compounds can vary over a broad range and can be controlled through the molar ratio of the reactants and the reaction conditions, especially the reaction time. When using higher molar amounts of the amine and aldehyde in the Mannich reaction along with longer reaction time, a mixture enriched in keto-diamine compounds is obtained. The molar ratio of keto-monoamine to keto-diamine compounds can spread from 95:5 to 5:95, preferably from 90:10 to 10:90 and the skilled person will select the amounts of reactants and the reaction conditions in a suitable manner depending on whether a mixture enriched in keto-monoamine compounds is desired or whether an excess of keto-diamine compounds is desired. Working examples 1 and 2 provide detailed information how the ratio of the two possible products can be controlled and adjusted.

In accordance with a preferred embodiment, the present invention relates to a mixture comprising a compound of formula (I) as defined above wherein X is represented by formula (II) and X' is hydrogen, and a compound of formula (I) as defined above wherein both X and X' are represented by formula (II), in particular a mixture of a compound of formula (I') and a compound of formula (I").

The molar ratio of the two compounds in the mixture may be in the range from 95:5 to 5:95, preferably in the range from 90:10 to 10:90, particularly preferred in the range from 20:80 to 80:20.

Mannich reactions are well known to the person skilled in the art who will select the suitable reaction conditions based on the professional knowledge and on the specific application situation and the substrates used.

Generally said, the reaction can be conducted in an autoclave. The internal ketone and an optional suitable solvent (e.g. methanol, ethanol, isopropanol, THF, methyl-THF, DMSO) are loaded into the reactor followed by the suitable amount of formaldehyde or other activating aldehyde (formaldehyde being preferably used in the form of a 37% w/w aqueous solution) and the suitable amount of ammonia or an amine of formula $NHR^1R^2$ ($R^1$ and $R^2$ having the meaning as defined in claim 1) (preferably in the form of its ammonium ($NH_4^+$) or protonated amine ($H_2NR^1R^{2+}$) salt, typically hydrochloride or hydrosulfate salt: $H_2NR^1R^2.Cl$ or $H_2NR^1R^2.HSO4$ respectively). An aqueous acid solution is also added as catalyst (in accordance with a preferred embodiment, concentrated aqueous hydrochloric acid may be used) and the resulting mixture is then heated to a temperature in the range from 50 to 250° C., preferably from 80 to 120° C. and the mixture is allowed to stir until the full conversion of the ketone is achieved. At the end of the reaction, the solvent is typically removed by distillation.

At the end of the Mannich reaction, the product may be obtained in the form of the protonated keto-amine salts notably in the case the amine reactant $NHR^1R^2$ has been used in the form of its protonated amine salt. The product can be used as such or the free keto-amine Mannich base can be recovered by deprotonation using a suitable base. As examples of suitable bases one can mention: NaOH, LiOH, KOH, $Na_2CO_3$, $NaOCH_3$, $NaOCH_2CH_3$ etc . . . The deprotonation can take place in a suitable solvent, such as for example: water, methanol, ethanol, isopropanol, DMSO, acetonitrile, THF, methyl-THF, diethyl ether, methyl tert-butyl ether, ethyl acetate, dioxane, toluene, xylene, $CH_2Cl_2$, $CHCl_3$ or their mixture. The deprotonation reaction can be conducted in a temperature range from from 0° C. to 100° C. The base can be used in stoichiometric or in an excess amount and the quantity of base can be adjusted in order to achieve a pH above 10.

Alternatively, instead of using formaldehyde, a reactant that is able to decompose in-situ into formaldehyde under the reaction conditions can be used in the process of the invention. In this case, the reactant can also act as the solvent and can be used in excess amounts with respect to the ketone. Therefore no additional solvent is needed. As example of such formaldehyde generating reactant we can mention: 1,3-dioxolane or dimethoxymethane.

To obtain the ionic compounds in accordance with the present invention, the products obtained after the Mannich reaction have to be alkylated or protonated.

Suitable reactions and the conditions thereof have been described in the literature and are known to the skilled person, so that no details need to be given here. The skilled person will select the suitable reactants and the reaction conditions based on his professional knowledge.

The amine obtained as a result of the Mannich reaction in the second step can be alkylated with an alkylating agent of general formula R"-L wherein L is a leaving group giving after alkylation an anion or an anionic group (such as e.g. methosulfate), preferably a dialkylsulfate, even more preferably dimethylsulfate (DMS), to obtain the target keto-ammonium compound of the present invention.

To a suitable amount of alkylating agent in a suitable solvent, a concentrated solution of the keto-amine in the same solvent is progressively added under stirring (usually at room temperature) at a rate avoiding significant temperature increase due to reaction exothermy.

After the end of the addition, the mixture is allowed to stir at room temperature (typically 15-30° C.) and the volatiles (mainly solvent and traces of alkylating agent (e.g. DMS)) are removed under vacuum to afford the final keto-ammonium compounds bearing substituents $R^1$ to $R^3$.

In accordance with a preferred embodiment, the protonation or alkylation is carried out under an inert atmosphere.

In a preferred protonation procedure, water and a suitable amount of an aqueous acid (e.g. hydrochloric acid) are added to a flask equipped with stirring means and a condenser. The solution thus obtained is stirred at a temperature preferably in the range from 0 to 10° C. and the product obtained from the Mannich reaction is then slowly added. If the viscosity of the system is too high, water can be added to reduce same.

The reaction mixture is stirred at a temperature preferably in the range from 5° C. to 100° C., more preferably in the range of from 10 to 50° C. until the reaction is completed. The water may be optionally removed e.g. through lyophilization to obtain the desired keto-ammonium compounds in accordance with the present invention.

By modifying the conditions of the alkylation or protonation reactions, the keto-diamine compounds (such as the non alkylated or non protonated precursor of compound I") obtained after the Mannich reaction can be converted to compounds of formula I wherein substituents X and X' form together a group of formula (III). Working example 3 provides detailed information in this regard. The skilled person will adjust the reaction conditions in an appropriate manner to steer the reaction towards the desired final compound.

During this cyclization reaction, one ammonium group of formula $—NR^1R^2R^3$, with the definitions of $R^1$ to $R^3$ provided above, belonging to one of the substituents X or X' acts as a leaving group. On the other hand, one amino group of formula $—NR^1R^2$ belonging to the other substituents X or X' acts as the nucleophile and undergoes a nucleophilic attack on the linking carbon of the group $CHR^x$ belonging to the other substituent X or X'. Such cyclization reaction is therefor favored when the alkylating agent or the acid used respectively to alkylate or protonate the keto-diamine substrate is used in an equimolar amount with respect to the keto-diamine substrate (meaning half an equivalent amount with respect to the amino groups of the keto-diamine substrate). Also the use of weaker acids (with pKa>1) such as carboxylic acids can favor the formation of the cyclized product upon heating in aqueous solutions.

Other processes than the combination of a Mannich reaction followed by alkylation or protonation may be suitable to synthesize the compounds in accordance with the present invention and the skilled person is aware of such processes so that it is not necessary to give further details here.

The compounds of the present invention can be used as surfactants. Surfactants are compounds that lower the surface tension (or interfacial tension) between two non miscible liquids, a liquid and a gas or between a liquid and a solid. Surfactants may act as detergents, wetting agents, emulsifiers, foaming agents, and dispersants.

Surfactants are usually organic compounds that are amphiphilic, meaning they contain both hydrophobic groups (their tails) and hydrophilic groups (their heads). Therefore, a surfactant contains both a water-insoluble (or oil-soluble) component and a water-soluble component. Surfactants will diffuse in water and adsorb at the interface between air and water or at the interface between oil and water, in the case where water is mixed with oil. The water-insoluble hydrophobic group may extend out of the bulk water phase, into the air or into the oil phase, while the water-soluble head group remains in the water phase.

The adsorption of a cationic surfactant on negatively charged surfaces is an important property for such surfactants. This property is usually linked to the minimum concentration of surfactant needed to produce aggregation of a negatively charged cellulose nanocrystal (CNC, which is often used as reference material)) suspension in aqueous media. Consecutive variation of size of aggregates can be monitored and followed by dynamic light scattering (DLS).

Following the protocol described in E. K. Oikonomou et al., J. Phys. Chem. B, 2017, 121 (10), 2299-307 the adsorption properties of the quaternary ammonium compounds can be investigated by monitoring the ratio X=[surfactant]/[CNC] or the mass fraction M=[surfactant]/([surfactant+[CNC]), at fixed [surfactant]+[CNC]=0.01 wt % in aqueous solution, required to induce the agglomeration of the cellulose nanocrystals.

The biodegradability of the compounds of the present invention can be determined in accordance with procedures described in the prior art and known to the skilled person. Details about one such method, OECD standard 301, are given in the experimental section hereinafter.

Should the disclosure of any patents, patent applications, and publications which are incorporated herein by reference conflict with the description of the present application to the extent that it may render a term unclear, the present description shall take precedence.

WORKING EXAMPLES

Example 1—Synthesis of a Mixture of Compounds of Formula I' and I" from $C_{31}$16-Hentriacontanone-Mixture Enriched in Compounds of Formula I'

Synthesis of Mixture of Ketoamine Compounds

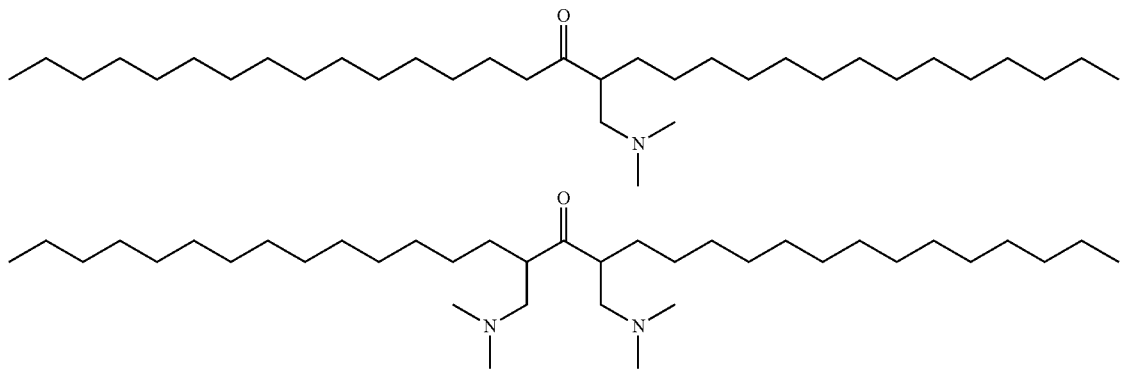

All the reactions were conducted in carefully dried vessels and under an inert argon atmosphere.

In a 1 L round bottom flask equipped with a condenser, a magnetic stirrer, a heater and a temperature probe were added:
- 70 g of 16-hentriacontanone (0.155 mol, 1 eq.)
- 45.22 g of dimethylamine hydrochloride (0.555 mol, 3.6 eq.)
- 330 mL of 1,3-dioxolane The mixture was allowed to stir at room temperature and 1.29 mL of aqueous HCl solution (37 wt %) (0.57 g HCl, 15.7 mmoles, 10 mol %) were carefully added into the reaction vessel. The mixture was then allowed to stir at 90° C. and the reaction progress was followed by NMR analysis.

After 8 h stirring at 90° C., the mixture was allowed to cool down to room temperature and an aqueous solution of NaOH (1M) was carefully added to the reaction crude under stirring until pH was above 11.

The product was then extracted three times with 350 mL of diethyl ether and the organic phase was washed five times with 350 mL of 0.5M NaOH solution.

The organic phase was dried over $MgSO_4$, filtered and the solvent was removed under vacuum to afford 78 g of crude material. At this stage the product mixture contained around 5 mol % of the methylenated keto-amine by-product which can converted to the keto-diamine following the procedure described below:

To the crude material in a 500 mL round bottom flask equipped with a mechanical stirrer, a condenser, a temperature probe and a heater, 150 mL of an aqueous dimethylamine solution (40 wt %) was added. The resulting mixture was stirred at 40° C. overnight.

NMR analysis showed complete conversion of the methylenated by-product to the desired keto-diamine.

To the crude mixture 350 mL of diethyl ether followed by 100 mL of water were added, the organic phase was separated and the aqueous phase was re-extracted twice with 350 mL of diethyl ether.

The organic phases were collected, washed several times with brine, dried over $MgSO_4$ and filtered. After solvent evaporation 64.85 g of crude material were recovered (Yield: 86%).

The mixture was stirred at room temperature during 5 h and after reaction completion water was removed by lyophilization to afford the ammonium salts mixture as a white fine powder (quantitative yield).

Example 2—Synthesis of a Mixture of Compounds of Formulae I' and I" Enriched in Compounds of Formula I"

Synthesis of a Mixture of Ketoamine Compounds

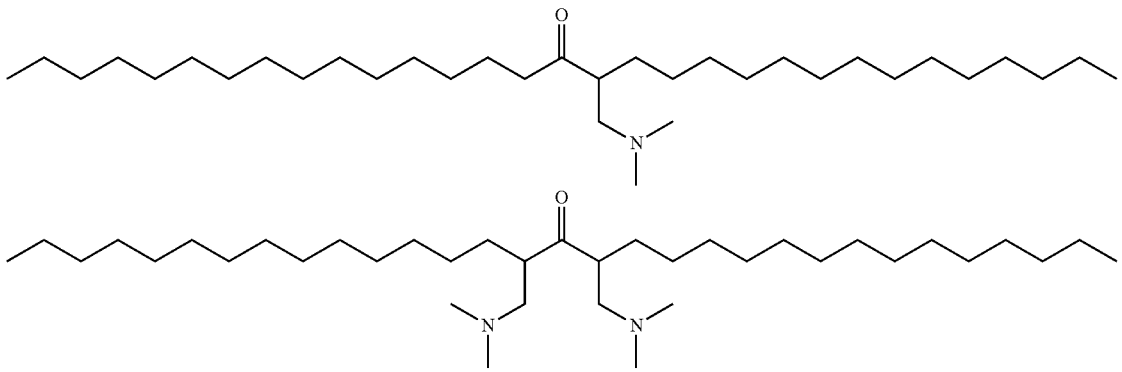

NMR analysis showed that the mixture contained 72 mol % of keto-monoamine and 21 mol % of keto-diamine.

1H NMR ($CDCl_3$ 400 MHz) δ(ppm): 2.82-2.70 (m, 2H, di-amine, both diastereoisomers), 2.69-2.58 (m, 1H, mono-amine), 2.54 (dd, J=11.6 Hz, J=9.2 Hz, 1H, mono-amine), 2.53-2.43 (m, 2H, di-amine, both diastereoisomers), 2.40 (dt, J=7.2 Hz, J=2.48 Hz, 2H, mono-amine), 2.17 (s, 12H, di-amine diastereoisomer 1), 2.16 (s, 12H, di-amine diastereoisomer 2), 2.15 (s, 6H, mono-amine), 2.13 (dd, J=11.6 Hz, J=5.2 Hz, 1H, mono-amine), 1.65-1.45 (m, 2H+4H, mono-amine+diamine), 1.40-0.95 (m, 50H+48H, mono-amine+di-amine), 0.86 (t, j=6.4 Hz, 6H mono-amine+di-amine).

$^{13}C$ NMR ($CDCl_3$, 101 MHz) δ (ppm): 216.6 (di-amine, diastereoisomer 1), 216.2 (di-amine, diastereoisomer 2), 214.46 (mono-amine), 62.24 (mono-amine), 61.48 (di-amine, diastereoisomer 1), 61.26 (di-amine, diastereoisomer 2), 51.04 (mono-amine), 50.40 (di-amine, diastereoisomer 1), 50.32 (di-amine, diastereoisomer 2), 46.12 (di-amine), 46.08 (mono-amine), 42.53 (mono-amine), 32.15, 30.75, 30.11, 29.98, 29.92, 29.89, 29.86, 29.80, 29.76, 29.71, 29.67, 29.59, 29.49, 27.77, 27.69, 27.63, 23.49, 22.92, 14.34 (terminal $CH_3$).

Protonation of Mixture of Ketoamine Compounds

The reaction was carried out under an inert argon atmosphere.

In a 1 L round bottom flask equipped with a condenser, a mechanical stirrer and a temperature probe 200 mL of water 14.0 g of an aqueous HCl solution (37 wt %) (0.142 mol) were added.

The solution was allowed to stir at 0° C. and the keto-amine mixture (64.85 g, 0.097 mol of mono-amine, 0.028 mol of di-amine, 1 eq.) was progressively added to the reaction vessel. An additional 200 mL of water was added in order to reduce the solution viscosity.

All reactions were conducted in carefully dried vessels and under an inert argon atmosphere.

In a 1 L round bottom flask equipped with a condenser, a magnetic stirrer, a heater and a temperature probe were added:

75 g of 16-hentriacontanone (0.166 mol, 1 eq.)
27.61 g of dimethylamine hydrochloride (0.339 mol, 2.04 eq.)
380 mL of 1,3-dioxolane.

The mixture was allowed to stir at room temperature and 1.82 mL of aqueous HCl solution (37 wt %) (0.81 g HCl, 22 mmoles, 13 mol %) were carefully added into the reaction vessel. The mixture was then allowed to stir at 90° C. and the reaction progress was followed by NMR analysis.

After two days of stirring at 90° C., the mixture was allowed to cool down to room temperature and an aqueous solution of NaOH (1M) was carefully added to the reaction crude under stirring until pH was above 11.

The product was then extracted with diethyl ether and the organic phase was washed several times with a 0.5 M NaOH solution.

The organic phase was dried over $MgSO_4$ filtered and the solvent was removed under vacuum to afford 87 g of crude material. At this stage the product mixture contained around 41 mol % of the methylenated keto-amine by-product which was converted to the keto-diamine following the procedure described below:

To the crude material in a 500 mL round bottom flask equipped with a mechanical stirrer, a condenser, a temperature probe and a heater, 150 mL of an aqueous dimethylamine solution (40 wt %) were added. The resulting mixture was stirred at 40° C. overnight.

NMR analysis showed complete conversion of the methylenated keto-amine by-product to the desired keto-diamine.

The product was extracted using diethyl ether and the organic phase was washed several times with brine followed by an aqueous NaOH (0.5M) solution.

The organic phase was dried over MgSO$_4$ and filtered. After solvent evaporation 82.5 g of crude material was recovered.

NMR analysis showed that the mixture contained 71 mol % of keto-diamine and 14 mol % of keto-monoamine (6 mol % of a methylenated keto-diamine by-product were also present).

Protonation of Mixture of Ketoamine Compounds

All the reactions were conducted in carefully dried vessels and under an inert argon atmosphere In a 500 mL round bottom flask equipped with a condenser, a mechanical stirrer and a temperature probe
65 mL of water
4.9 g of an aqueous HCl solution (37 wt %) (0.050 mol) were added.

The solution was allowed to stir at 0° C. and the ketoamine mixture (15.04 g, 4.4 mmol of mono-amine, 22.6 mmol of di-amine, 1.82 mmol of methylenated diamine, 1 eq.) was progressively added into the reaction vessel. An additional 100 mL of water was added in order to reduce the solution viscosity.

The mixture was stirred at room temperature during 18 h and after reaction completion water was removed by lyophilization to afford the ammonium salts mixture as a white fine powder (quantitative yield).

Example 3—Synthesis of Compound of Formula I'''

A mixture of keto-amines enriched in compounds of formula I''' was synthetized according to the protocol described in Example 2.

The mixture obtained had the following composition:
71 mol % of keto-diamine
14 mol % of keto-monoamine
6 mol % of a methylenated keto-diamine.

In a 500 mL round bottom flask equipped with a magnetic stirrer, a heater and a temperature probe and under an inert argon atmosphere
73.97 g of the ketone-amine mixture with the composition above (111 mmoles of diamine, 22 mmoles of monoamine, 9 mmoles of methylenated diamine), and
125 mL of isopropanol were added.

The mixture was allowed to cool down to 10° C. and citric acid (23.46 g, 122 mmoles) was progressively added into the reaction vessel.

At the end of the addition the mixture was allowed to stir at room temperature overnight and isopropanol was removed under vacuum to afford the crude material as an orange paste. At this stage the crude contained a certain amount of dimethylammonium salts which were removed following the work-up described below.

The crude residue was re-dissolved in diethyl ether containing 3 vol % of isopropanol and the formed precipitate was removed through filtration. The filtrate was then washed 2 times with an aqueous solution of sodium citrate (0.5 M) (previously formed by the neutralization of citric acid with one equivalent of NaOH).

The organic phase was then evaporated to afford 59.91 g of quaternary keto-ammonium compound as a beige powder. Yield: 66%
NMR Data
$^1$H NMR (CDCl$_3$-MeOD 400 MHz) δ(ppm): 3.88-3.70 (m, 2H), 3.55-3.40 (m, 2H), 3.49 (s, 3H), 3.26 (s, 3H), 3.02-2.88 (m, 2H), 2.81 (d, J=15.6 Hz, 2H), 2.73 (d, J=15.6 Hz, 2H), 1.92-1.72 (m, 2H), 1.45-1.00 (m, 50H), 0.86 (t, J=6.8 Hz, 6H).

$^{13}$C NMR (CDCl$_3$-MeOD, 101 MHz) δ(ppm): 204.17, 178.25, 173.60, 72.42, 66.74, 56.13, 48.33, 43.82, 31.79, 29.60, 29.52, 29.50, 29.43, 29.26, 29.21, 26.65, 26.62, 25.70, 25.59, 22.50, 13.59 (terminal CH$_3$).

Example 4—Evaluation of Adsorption Properties on Nanocellulose Crystals

Adsorption of cationic surfactant on negatively charged surface is an important property for various applications. This property is linked to the minimal concentration of cationic surfactant needed to produce aggregation of negatively charged cellulose nano crystal (CNC) in suspension in aqueous media. Comparison of the aggregate size can be monitored by dynamic light scattering (DLS).

Following the protocol described in literature (Ref.: E. K. Oikonomou, et al., J. Phys. Chem. B, 2017, 121 (10), pp 2299-2307), adsorption properties of quaternary ammonium were investigated by monitoring the ratio X=[surfactant]/[CNC] or the mass fraction M=[surfactant]/([surfactant]+[CNC]), at fixed [surfactant]+[CNC]=0.01 wt % in aqueous solution, required to induce the agglomeration of the cellulose nano crystal.

The range of CNC aggregation correspond to the range of ratio X (or M) triggering an aggregation of CNC, i.e. the range where the aggregate size measured by DLS is higher than a pure aqueous solution of CNC or an aqueous solution of surfactant at 0.01 wt %.

Ranges of X and M of aggregation of CNC are summarized in Table 1 (The CNC that was used for those measurements had mean diameter of 104.6+/−4.8 nm with a poly-dispersity index of 0.20). The lower range of aggregation X or M, the better the adsorption properties on negatively charged surface.

TABLE 1

| Compound of | Range of CNC aggregation (Ratio) X = [surfactant]/[CNC] $X_{min}$-$X_{max}$ | Range of CNC aggregation (Mass fraction) $M_{min}$-$M_{max}$ |
|---|---|---|
| Fentacare ® TEP [1] | 0.1-<1* | 0.09-<0.5* |
| Example 1 | 0.05-1.7 | 0.05-0.6 |
| Example 2 | 0.02-<1* | 0.02-<0.5 |
| Example 3 | 0.02-1 | 0.02-0.5 |

[1]Fentacare® TEP was used as a comparison. Fentacare® TEP is a commercial surfactant representing the benchmark.

The data show that the surfactant properties of the compounds in accordance with the present invention (examples 1 to 3) are superior compared to the commercial surfactant Fentacare® TEP, giving aggregation at lower surfactant concentrations.

Example 5—Determination of Biodegradablilty

Biodegradability of the test substances has been measured according to the 301 F OECD protocol.

A measured volume of inoculated mineral medium, containing a known concentration of the test substance in order to reach about 50 to 100 mg ThOD/l (Theoretical Oxygen Demand) as the nominal sole source of organic carbon, was stirred in a closed flask (Oxitop™ respirometric flask) at a constant temperature (20±2° C.) for up to 28 days. Oxitop™ respirometric bottles were used in this test in order to access the biodegradability of the test samples: sealed culture BOD flasks were used at a temperature of 20±2 C during 28 days.

Evolved carbon dioxide was absorbed by pellets of Natrium or Potassium hydroxide present in the head space of the bottle. The amount of oxygen taken up by the microbial population (=oxygen consumption expressed in mg/l) during biodegradation process (biological oxidation of the test substance) decreased the pressure of the head space (Δ P measured by the pressure switch) and was mathematically converted in mg $O_2$ consumed/litre. Inoculum corresponded to a municipal activated sludge washed in mineral medium (ZW media) in order to decrease the DOC (Dissolved Oxygen Carbon) content. Control solutions containing the reference substance sodium acetate and also toxicity control (test substance+reference substance) were used for validation purposes. Reference substance, sodium acetate, has been tested in one bottle (at a nominal concentration of 129 mg/l corresponding to 100 mg ThOD/l) in order to check the viability of the inoculum. Toxicity control corresponds to the mixture of the substance reference and the test substance; it will check if the test substance is toxic towards the inoculum (if so, the test has to be redone at a lower test substance concentration, if feasible regarding the sensitivity of the method).

As the substances of the present invention are for a majority of them not very soluble in water (if some are soluble in water, their metabolite after hydrolysis containing the alkyl chain has often very low solubility in water), we used a specific protocol named the "emulsion protocol". This protocol enabled us to increase the bioavailability of the poorly water soluble substance in the aqueous phase where we had the inoculum.

Emulsion protocol consisted of adding the test substance in the bottle through a stock solution made in an emulsion.

Emulsion was a 50/50 v/v mixture of a stock solution of the test substance dissolved in a non-biodegradable surfactant (Synperonic® PE 105 at 1 g/l) and then mixed with a mineral silicone oil AR 20 (Sigma).

The first dissolution of the test substance in the non-biodegradable surfactant solution often required magnetic stirrer agitation followed by ultrasonication.

Once the dissolution was made, we mixed the aqueous solution with a mineral silicone oil at a 50/50 volume/volume ratio. This emulsion was maintained by magnetic stirrer agitation and was sampled for an addition in the corresponding bottle in order to reach the required test substance concentration.

Two emulsion controls were run in parallel during the test in order to remove their value from the emulsion bottle containing the test substance added through the emulsion stock solution.

The results of the biodegradability test are summarized in Table 2

| Compound of | Biodegradability after 28 days |
| --- | --- |
| Example 1 | 51% (OECD 301F) |
| Example 2 | 30% (OECD 301F) |

The results show that the compound of example 1 has the best biodegradability amongst the compounds used in the working examples.

Overall, the compounds of the present invention usually show a good combination of surfactant properties combined with a reasonable to good biodegradability—a combination which is in many cases not achieved by commercial cationic surfactants.

Since the compounds of the present invention are also easily available starting from internal ketones which are easily accessible from fatty acids or fatty acid derivatives, the compounds of the present invention also provide economical benefits over the prior art compounds.

The invention claimed is:

1. An ionic compound of general formula I

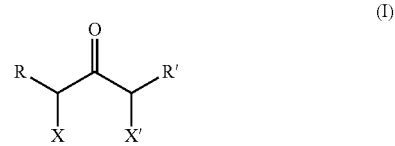

wherein R and R', which may be the same or different at each occurrence, are a $C_4$-$C_{27}$ aliphatic group, X is a monovalent radical represented by formula (II)

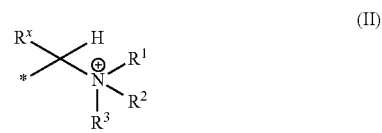

wherein $R^1$ and $R^2$, which may be the same or different, are hydrogen or a $C_1$ to $C_4$ alkyl group, $R^3$ is hydrogen, $R^x$ is hydrogen or an aliphatic group of 1 to 6 carbon atoms, and wherein * denotes the position through which the monovalent radical is bound to the rest of the ionic compound X' is hydrogen or is a monovalent radical represented by formula (II) or wherein X and X' together form a divalent radical of formula (III)

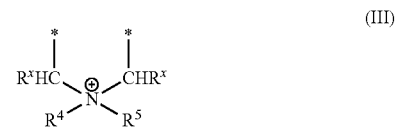

wherein $R^x$, which may be the same or different, are hydrogen or an aliphatic group with 1 to 6 carbon atoms, and $R^4$ and $R^5$, which may be the same or different, are hydrogen or a $C_1$ to $C_4$ alkyl group, and wherein * denote the positions through which the divalent radical is bound to the rest of the ionic compound.

2. The compound in accordance with claim 1 wherein X is a monovalent radical represented by formula II and X' is hydrogen.

3. The compound in accordance with claim 1 wherein X is a monovalent radical represented by formula II and X' is a monovalent radical represented by formula (II).

4. The compound in accordance with claim 1 wherein X and X' form together a divalent radical of formula (III).

5. The compound in accordance with claim 1 represented by any of formulae I', I" and

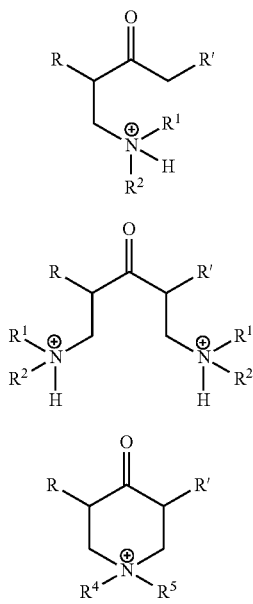

wherein R, R', R¹, R², R⁴ and R⁵ have the meaning as defined in claim 1.

6. The compound in accordance with claim 1 wherein R¹, R², R⁴ and R⁵ are a $C_1$ to $C_4$ alkyl group.

7. The compound in accordance with claim 1 wherein R¹, R², R⁴ and R⁵ are methyl.

8. The compound in accordance with claim 1 wherein the aliphatic groups R and R' have from 6 to 24 carbon atoms.

9. The compound in accordance with claim 8 wherein the aliphatic groups R and R' have from 8 to 20 carbon atoms.

10. The compound in accordance with claim 1 wherein the aliphatic groups R and R' are independently chosen from alkyl and alkenyl groups, preferably from alkyl groups.

11. A mixture comprising a first compound of formula I in accordance with claim 1 wherein X is represented by a group of formula II and X' is hydrogen and a second compound of formula I in accordance with claim 1 wherein both X and X' are represented by a group of formula II.

12. The mixture in accordance with claim 11 wherein the molar ratio of the two compounds is in the range of from 90:10 to 10:90.

13. The mixture in accordance with claim 11 comprising a compound of formula I' and a compound of formula I" as defined in claim 5.

14. An electroneutral compound of general formula (IV)

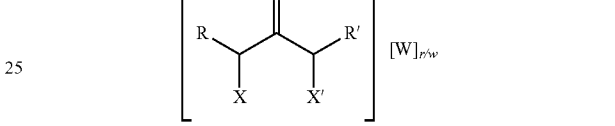

wherein R, R', X and X' are as defined in claim 1, W is an anion or an anionic group bearing w negative charges and r is the number of substituents X and X' which are represented by formula (II) or (III).

* * * * *